US005679649A

United States Patent [19]

Fukunaga

[11] Patent Number: 5,679,649
[45] Date of Patent: Oct. 21, 1997

[54] USE OF ADENOSINE COMPOUNDS FOR AUTONOMIC NERVOUS SYSTEM ATTENUATION

[76] Inventor: Atsuo F. Fukunaga, 5411 Little Bow Rd., Rancho Palos Verdes, Calif. 90274

[21] Appl. No.: 458,981

[22] Filed: Jun. 2, 1995

Related U.S. Application Data

[62] Division of Ser. No. 437,080, May 5, 1995, which is a continuation of Ser. No. 203,670, Feb. 28, 1994, abandoned, which is a continuation of Ser. No. 83,214, Jun. 25, 1993, abandoned, which is a continuation of Ser. No. 756,480, Sep. 9, 1991, abandoned, which is a continuation-in-part of Ser. No. 521,529, May 10, 1990, abandoned.

[51] Int. Cl.$^6$ .................................................. A61K 31/70
[52] U.S. Cl. .................... 514/46; 514/47; 536/26.23; 536/26.26; 536/26.7; 536/27.6
[58] Field of Search ...................... 514/46, 47; 536/26.23, 536/26.26, 26.7, 27.6

[56] References Cited

U.S. PATENT DOCUMENTS

| | | |
|---|---|---|
| 4,605,644 | 8/1986 | Foker ........................................ 514/45 |
| 4,673,563 | 6/1987 | Berne et al. ............................... 514/46 |
| 4,755,594 | 7/1988 | Bridges et al. ........................ 536/27.62 |
| 4,880,783 | 11/1989 | Mentzer, Jr. et al. ..................... 514/46 |
| 4,880,918 | 11/1989 | Rapaport .................................... 514/47 |
| 5,049,372 | 9/1991 | Rapaport .................................. 424/1.77 |
| 5,104,859 | 4/1992 | Sollevi ...................................... 514/46 |

FOREIGN PATENT DOCUMENTS

| | | |
|---|---|---|
| 0301900 | 2/1989 | European Pat. Off. . |
| 0797237 | 6/1958 | United Kingdom . |
| 8701593 | 3/1987 | WIPO . |
| 8802258 | 4/1988 | WIPO . |

OTHER PUBLICATIONS

Fukunaga et al.(I), "ATP Induced Hypotensive Anesthesia During Surgery," *Anesthesiology*, 57, A65 (1982).
Fukunaga et al.(II), "Hypotensive Effects of Adenosine and Adenosine Triphosphate Compared with Sodium Nitroprusside," *Anesthesiology*, 61(3), 273–278 (1982).
Dunwiddie et al., "Sedative and Anticonvulsive Effects of Adenosine Analogs in Mouse and Rat," *J. Pharm. and Expert Therapeutics*, 220, 70–76 (1982).
Seitz et al., "Adenosine Reduces Halothane MAC in Dogs," *Anesthesiology*, 68, A263 (1989).
Homeister et al., "Combined Adenosine and Lidocaine Administration Limits Myocardial Reperfusion Injury," *Circulation*, 82(2), 595–608 (1990).
Gomma, "Characteristics of Analgesia Induced by Adenosine Triphosphate," *Pharmacology and Toxicology*, 61, 199–202 (1987).
Drury et al., "The Physiological Activity of Adenine Compounds with Especial Reference to Their Action Upon the Mammalian Heart," *J. Physiology(Cambridge, England)*, 68, 213–237 (1929).
Vapaatalo et al., "Stereospecificity in Some Central and Circulatory Effects of Phenylisopropyladenosine (PIA)," *Arzneim. Forsch. (Drug Res.)*, 25(3), 407–410(1975).

Phillis et al.(I), "Roles of Adenosine and Adenine Nucleotides in the Central Nervous System," in *Physiology and Pharmacology of Adenosine Derivatives*, Daly et al. eds., Raven Press, New York, 1983, pp. 219–235.
Phillis et al.(II), "Evidence for an $A_2$–like Receptor on Cerebral Cortical Neurons," *J. Pharm. Pharmacol.*, 34, 453–454 (1982).
Nunn et al., "Introduction," in *General Anesthesia*, 5th Ed., Nunn et al. eds., Butterworth, London, 1989, pp. 1–6.
Ohisalo et al., "Regulatory Functions of Adenosine," *Medical Biology*, 65, 181–191 (1987).
Williams, "Tissue and Species Differences in Adenosine Receptors and Their Possible Relevance to Drug Development," in *Adenosine: Receptors and Modulation of Cell Function*, Stefanovich et al. (eds.), IRL Press Ltd., Oxford, UK, 1985, pp. 73–84.
Stoelting et al. (eds.), *Principles of Anesthesia*, 2nd Ed., Churchill Livingstone, New York, NY, 1989, pp. 115–119.
Katzung (ed.), *Basic & Clinical Pharmacology*, Ch. 24, Appleton & Lange, Norwalk, Connecticut, 1995, pp. 381–394.
Seitz et al., "Adenosine Decreases the Minimum Aveolar Concentration of Halothane in Dogs," *Anesthesiology*, 73, 990–994 (1990).
Orwall et al., "Clinical Experience with Adenosine for Controlled Hypotension During Cerebral Aneurysm Surgery," *Anesthesiology and Analgesia*, 66, 229–234 (1987).
Williams, "Purine Receptors in Mammalian Tissues: Pharmacology and Functional Significance," *Ann. Rev. Pharmacology & Toxicology*, 27, 315–345 (1987); see particularly pp. 316, 328–329 and 335 refer to hypnotic effects.
Haulica et al., "Preliinary Data on the Possibel Hypnogenic Role of Adenosine," *J. Neurochem.*, 21, 10–19–1020 (1973).
Birch et al., "L–phenylisopropyladenosine (L–PIA) Diminishes Halothane Anesthetioc Requirements and Decreases Neurotransmission in Rats," *Life Science*, 42(14), 1355–1360 (1988); p. 1355, second paragraph, lines 5–7.
Conradson et al., "Cardiovascular Effects of Infused Adenosine: Potentiation by Dipyridamole," 129, 387–391 (1987).
Eger et al., "Minimum Aveolar Anesthetic Concentration [MAC]: A Standfard of Anesthetic Potency," *Anesthesiology*, 26, 756–763 (1965).
Snyder, "Adenosine as Neuromodulator," *Ann. Rev. Neuroscience*, 8, 103–124 (1985); see pp. 108 & 119, second paragraphs.
Bloor et al., "Reduction of Halothane Anesthetic Requirement by Clonidine, an Alpha–Adrenergic Agonist," *Anesthesia and Analgesia*, 61, 741–745 (1982).

(List continued on next page.)

*Primary Examiner*—John Kight
*Assistant Examiner*—L. Eric Crane
*Attorney, Agent, or Firm*—Fulwider Patton Lee & Utecht, LLP

[57] ABSTRACT

A method of inducing anesthesia, sedation, analgesia, hypothermia, and reduced stress by administering an effective amount of an adenosine compound to a mammal. It also provides a method for preserving donor organs in vivo by contacting them with an adenosine compound, as well as a method for preparing organ recipients for transplant.

5 Claims, 9 Drawing Sheets

OTHER PUBLICATIONS

Maze et al., "Anesthetic and Hemodynamic Effects of the Alpha$_2$–Adrenergic Agoinst, Azepexole, in Isoflurane–Anesthetized Dogs," *Anesthesiology*, 68(5), 689–694 (1988).

Segal et al., "Dexmedetomidine Diminishes Halothane Anesthetic Requirements in Rats Through a Post Synaptic Alpha$_2$ Adrenergic Receptor," *Anesthesiology*, 68(6), 818–823 (1988); see particularly col. 2 of p. 818, last paragraph.

Tanifuji et al., "Effect of Arterial Hypotension on Anesthetic Requirements in Dogs," *British J. Anesthesiology*, 48(10), 947–951 (1976).

Dunwiddie, "The Physiological Role of Adenosine in the Central Nervous System," *International Reviews in Neurobiology*, 27, 63–139 (1985); see particularly pp. 95–99, 121 and 126–128.

Feldberg et al., "Injection of Drugs into the Left Ventricle of the Cat," *J. Physiology London*, 123, 148–167 (1954).

Radulovacki et al., "Hypnotic Effects of Deoxycoformycin in Rats," *Brain Research*, 27, 271, 392–395 (1983).

Jonzon et al., "Modulation of Neurotransmission by Purine Nucleosides and Nucleotides," *Life Science*, 1984, 1971–1979.

Galloway et al., "Clonidine Prevents Methylxanthine Stimulation of NE Metabolism in Rats," *J. Neurochemistry*, 40, 246–251 (1983).

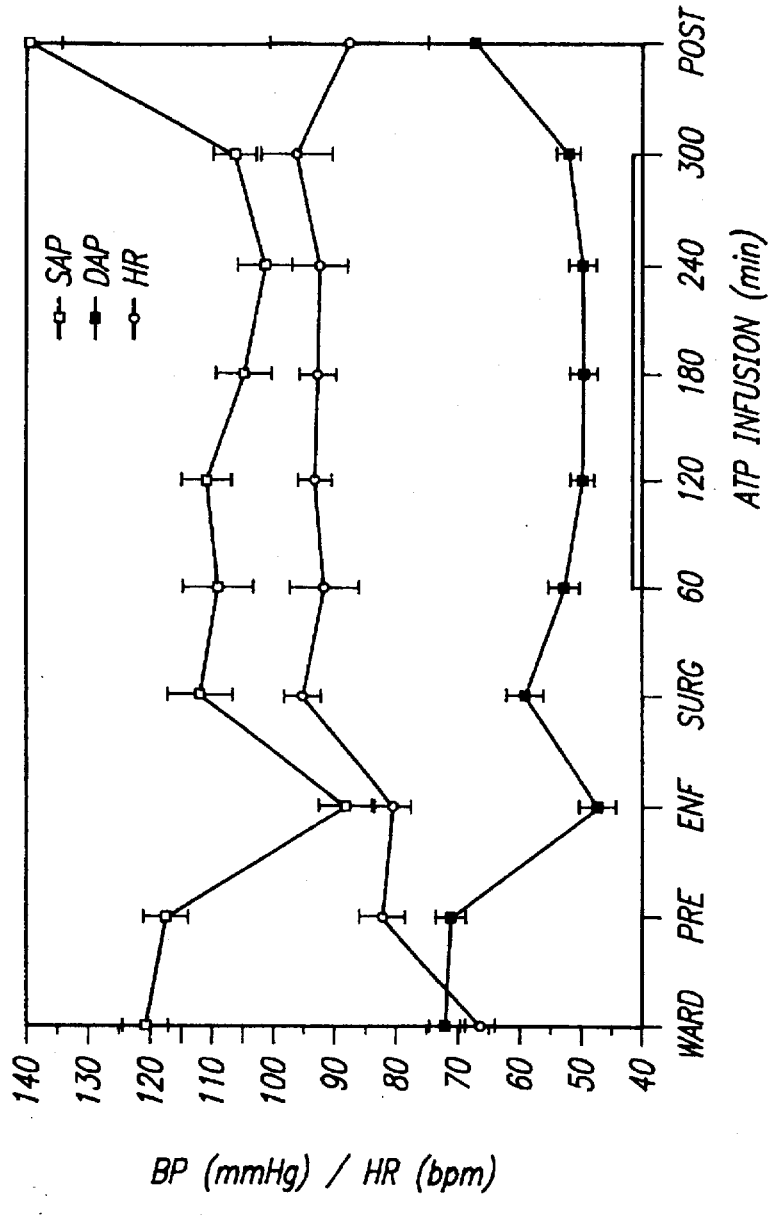

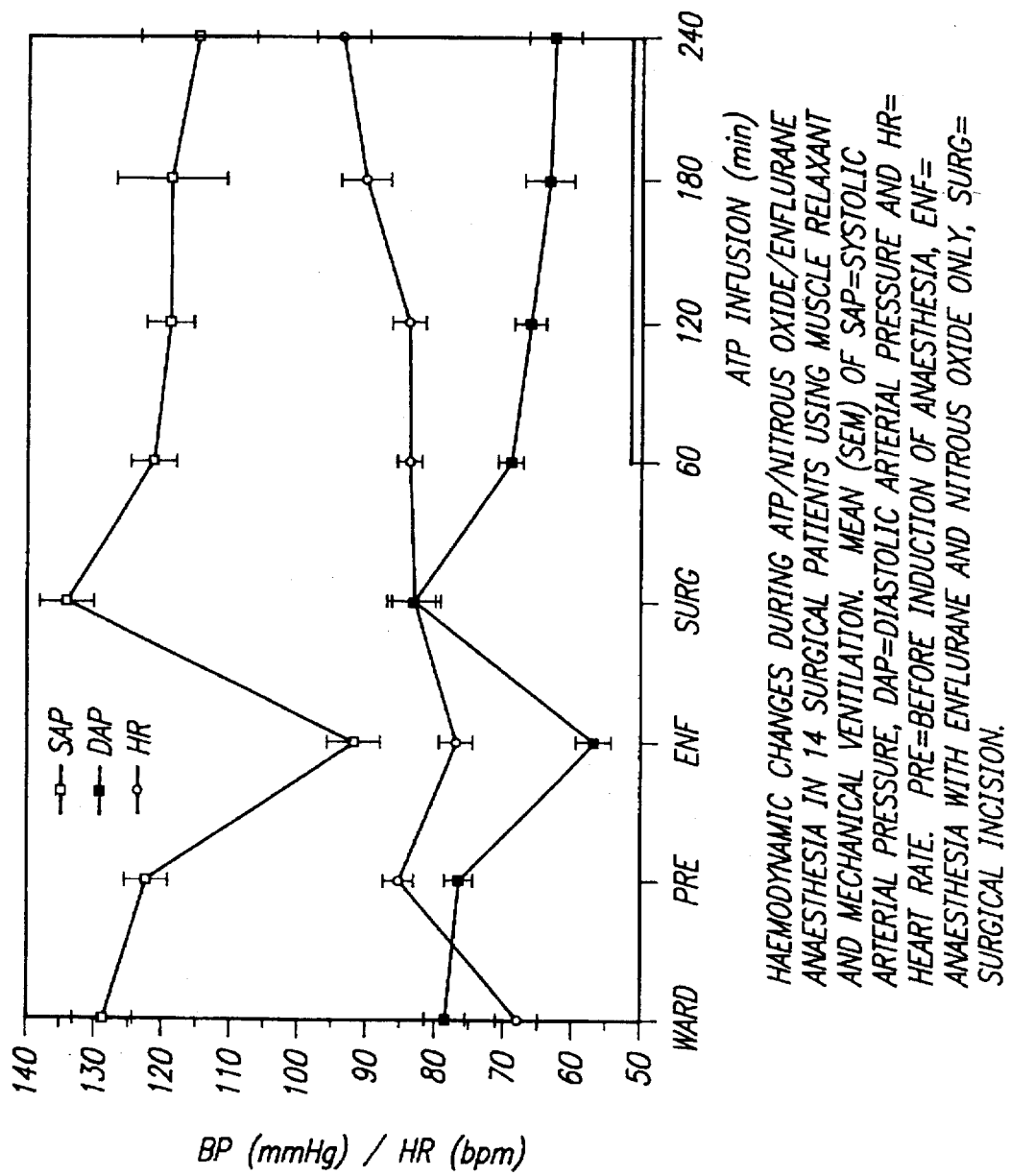

USE OF ADENOSINE COMPOUNDS FOR AUTONOMIC NERVOUS SYSTEM ATTENUATION

This application is a divisional of U.S. application Ser. No. 08/437,080, filed May 5, 1995, which is a continuation of U.S. application Ser. No. 08/203,670, filed Feb. 28, 1994, now abandoned, which is a continuation of U.S. application Ser. No. 08/083,214, filed Jun. 25, 1993, now abandoned, which is a continuation of U.S. application Ser. No. 07/756,480, filed Sep. 9, 1991, now abandoned, which is a continuation-in-part of U.S. application Ser. No. 07/521,529, filed May 10, 1990, now abandoned.

BACKGROUND OF THE INVENTION

1. Field of the Invention

This invention relates to a method of using adenosine compounds to induce anesthesia, sedation, analgesia, hypothermia, and to ameliorate stress.

2. Related Art

A patient is protected from the pain and stress of surgery and similar procedures by anesthesia which allows the maintenance of physiological homeostasis.

Adenosine has a variety of extracellular effects. It is known to have potent vasodilating, blood pressure lowering (hypotensive) and shock-inducing effects, but has never been demonstrated to have anesthetic activity when used clinically. Furthermore, the conventional wisdom is that neither adenosine nor adenosine triphosphate (hereinafter ATP), an adenine nucleotide, circulating in the blood, will cross the blood brain barrier. Therefore, despite analgesic and sedative effects suggested by previous studies in laboratory experiments, neither adenosine nor ATP had ever been thought to be suitable as anesthetics. A major problem with prior studies is that they were performed under such poorly controlled conditions that the vital signs: circulatory, such as blood pressure, heart rate and respiratory functions were not measured. Because data on the behavior of these parameters are essential in determining therapeutic efficacy, these studies failed to teach whether such potential analgesic and sedative effects were caused by the profound effects of these compounds on cardiovascular function, namely: hypotension, coma, bradycardia, or shock. Failure to determine the vital signs, and to isolate the analgesic properties from the coma or shock, which may be produced by potent hypotensive effects of adenosine, render these reports fatally flawed as teaching analgesia or sedation caused by adenosine. Consequently, previous studies do not evaluate usage for treatment purposes of these agents. Based on previous reports, such effects (analgesia, sedation) could not possibly have been translated to clinical applicability.

A variety of drugs are presently used to provide anesthesia. Goodman and Gilman's *The Pharmacological Basis of Therapeutics*, 7th Ed., 1985, MacMillan, N.Y., Chapters 13 and 14 provide an overview of the field of anesthesiology as currently understood by those skilled in the art.

Total replacement or dose reduction of other anesthetics have definite clinical advantages such as decreased toxicity and rapid recovery from anesthesia. These advantages can be realized because inhalational or other synthetic chemical anesthetics are often toxic even when used at the required effective dose and can produce severe cardio-respiratory and metabolic side effects. Secondly, the amount of anesthetic actually being used by the patient is subject to guesswork in the operating room.

Adenosine and ATP are endogenous compounds and, as a consequence, are unlikely to produce toxic effects. Both adenosine and ATP are known to be rapidly metabolized and eliminated from the blood stream; when the infusion is stopped, recovery starts immediately and proceeds rapidly. Therefore, either adenosine, ATP, or functionally similar adenosine compounds would be ideal replacements for inhalational anesthetics, and replacements for opioid analgesics.

In the present invention, it has been possible to isolate and demonstrate the intrinsic anesthetic properties of adenosine compounds. Applicant has found that under normal blood pressure and normal metabolic and respiratory functions, administration of an adenosine compound, such as adenosine and ATP, produced potent analgesic, sedative, and stress inhibiting effects, such as antihypertension and blood pressure control. Furthermore, such administration ameliorated undesirable cardiovascular and respiratory functions deteriorated by other anesthetics during anesthesia indicating that such adenosine compounds are superior anesthetic agents. This finding is unexpected and surprising because these agents are known to be potent hypotensive, bradycardic, and shock-inducing agents which clinicians would try to avoid.

Furthermore, when a subject anesthetized with an adenosine compound is then subjected to body temperature decrease, the decrease is not accompanied by shivering, cardiovascular distress, or pulmonary distress. This effect holds for drops in body temperature at least as large as 10° C. to 20° C.

Adenosine compounds have also been discovered to provide excellent blood and tissue oxygenation. As such, an adenosine compound can be used to maintain donor organs for transplant in the best possible condition while still in the donor body and the period of time between removal from the donor body and implantation. Furthermore, the excellent blood and tissue oxygenation induced by the adenosine compound can be used to maintain the organ and the organ recipient in the best possible condition.

SUMMARY OF THE INVENTION

This invention provides a method of inducing anesthesia, sedation, hypothermia, and analgesia, and a method of treating stress and hypothermia by administering an effective amount of an adenosine compound to a mammal in need of anesthesia or analgesia, or requiring induction of, or relief from, hypothermia. It also provides a method for preserving donor organs in vivo by contacting them with an adenosine compound, as well as a method for preparing organ recipients for transplant.

An aspect of this invention is a method of anesthetizing a mammal comprising administering an adenosine compound for the period that anesthesia is desired.

A further aspect of this invention is a method of creating subnormal body temperatures in a mammal comprising: (1) administering an adenosine compound; (2) exposing the body of the mammal to a sub-normal temperature ambient temperature; (3) allowing the body temperature of the mammal to fall; and (4) rewarming the mammal to normal body temperature.

Yet a further aspect of this invention is a method of relieving pain comprising administering an analgesically effective amount of an adenosine compound to a mammal for the period of time during which pain relief is desired.

Another aspect of this invention is a method of relieving stress, and stress response by administering an adenosine compound for the period of time during which stress and stress response relief is desired.

Another aspect of this invention is a method of providing in vivo preservation of donor organs, as well as organ transplant recipients, by maintaining good tissue oxygenation to the mammal and the organs, comprising the administration of an adenosine compound for a period pre and post-organ transplantation.

A further aspect of the invention is a method of sedating a mammal which comprises administering an adenosine compound for the period of time during which sedation is desired.

BRIEF DESCRIPTION OF THE DRAWINGS

FIG. 6 is a graphical comparison of the effect of stress on blood and tissue oxygen levels.

FIG. 9 shows hemodymic stability in surgical patients undergoing ATP anesthesia.

FIG. 10 shows the effects of ATP in decreasing enflurane requirements in surgical patients.

DETAILED DESCRIPTION OF THE PREFERRED EMBODIMENT

Figure 1:
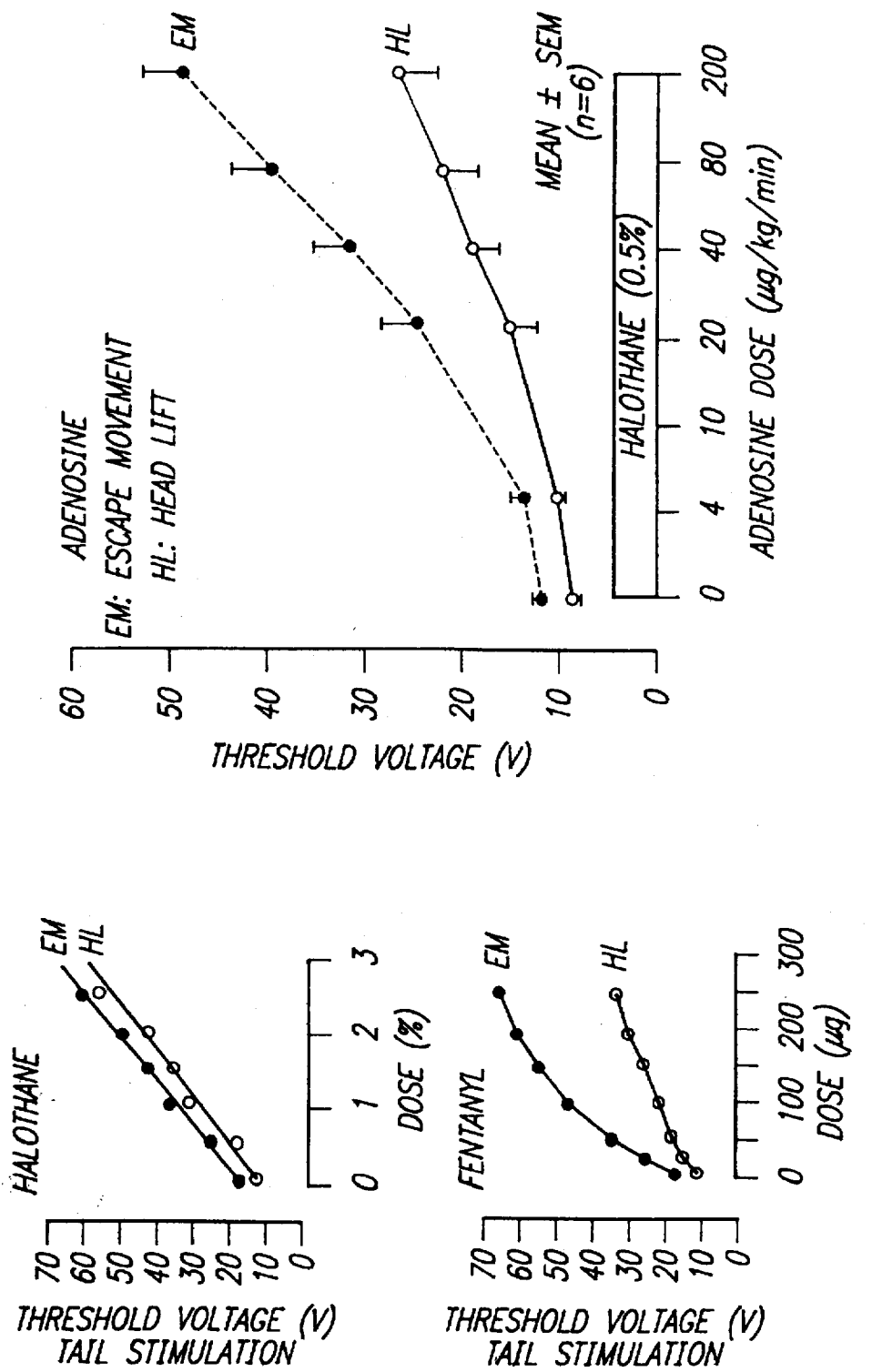
FIG. 1 compares the anesthetic effects of various agents by measuring hypnotic and analgesic responses.

As used herein, "anesthesia" is defined as the final result of several interacting, but independent effects. The first effect is sedation and/or sleep induction; the second is analgesia or pain relief;, the third is stress reduction to preserve physiological homeostasis, most frequently seen as blood pressure and heart rate modification during surgery; and finally, the fourth is usually considered to be muscle relaxation, particularly relaxation of skeletal muscle. At the present time, no single agent provides adequate levels of each and all of these four effects with an acceptable margin of safety, so combinations of drugs must be used in cases like surgery. Anesthetic as used herein will refer to any single drug that gives rise to at least two of the four effects.

The term "adenosine compound" denotes compounds such as adenosine and adenine nucleotides, as well as derivatives and analogs of adenosine and ATP. As used herein, the "adenine nucleotides" are adenosine monophosphate, adenosine diphosphate, and adenosine triphosphate. In general, the preferred adenine nucleotide is adenosine triphosphate (ATP).

As used herein, "surgery" and "surgical procedures" refer broadly to invasive discomfort-producing medical procedures. Included in the definition are such procedures as endoscopy, angiography, dental work, such as tooth extractions, as well as what is traditionally thought of as surgery, for example, appendectomies and the like. Also included in this definition is the presurgical phase and the post-surgical phase as well as, for example, the emergency room, the intensive care unit, and the like. As used herein, the terms broadly encompass the physiopathological states involving alteration in existing rhythmical processes that are homeostatic in nature.

Adenosine or its stable analogues can be administered by standard methods of administration, including but not limited to intravascular injections, intramuscular injections, oral ingestion via tablets, capsules or liquids, suppository implantations, inhalation, transdermal, nasopharyngeal, or mucosal absorption, or by continuous infusion utilizing biodegradable or non-biodegradable implantable devices. Any method of administration that is able to provide a plasma level effective to result in anesthetic, analgesic, sedative, hypothermic, or stress relief effects are suitable for the present invention.

"Continuous infusion" refers to intravascular infusions, intrathecal infusions, and like methods of providing a continuous drug dosage over a period of time. Continuous infusion can also be achieved utilizing a biologically-compatible device such as a manual or continuous pump system or an in vivo insertable chemical matrix containing the adenosine compound.

The method of the invention allows those skilled in the art to induce various physiological states using adenosine compounds. Many of these states are associated with providing relief from pain. The particular state induced to relieve pain can vary from a diminished awareness or perception of pain (e.g., analgesia) where there can be complete consciousness to a state where there is grogginess (e.g., sedation), to a state where there is a loss of consciousness (e.g., general anesthesia). Anesthesia can be further characterized as regional or local, where there is consciousness, but no awareness or sensation of pain. In the methods of the present invention, terms such as "anesthetically effective", "analgesically effective", and "sedatively effective", are used to describe that dose of adenosine compound needed to induce such states while maintaining the circulatory, respiratory, and metabolic functions within normal ranges. Those of skill in the art understand the appearance of these various states and know when a patient's functions are within the normal ranges. Thus, by monitoring the vital signs, the clinician can determine the state of the patient.

As used herein, "stress" refers to the physiological changes that accompany trauma such as surgery and physiopathological states involving alterations in existing rhythmical processes which are homeostatic in nature. It includes release of catecholamines, induction of hypertension, hypotension, vasoconstriction, vasodilation, and the like. The term "inhibitorally effective amount" when applied to stress refers to the concentration of adenosine compounds which is administered to inhibit, or lessen, the stress response within normal ranges of the circulatory and respiratory functions.

The present invention arose from the discovery that anesthesia, analgesia, sedation, and stress response inhibition could be induced by adenosine compounds independently of the profound hypotensive effects associated with these agents. However, this conclusion was reached after careful investigation which required the development of an experimental methodology that allowed the investigator to "dissect" the various anesthetic effects of adenosine while simultaneously monitoring the vital signs. The conventional tail clamping technique (standard method used to test anesthetic potency) has limitations and cannot establish the selectivity of the anesthetic responses by adenosine compounds. That method includes tactile, pulling, propioceptive as well as pain stimulation, and cannot assess the responses to stimuli in a more specific manner. By using the electrical stimulation methodology, it was possible to differentiate the arousal (hypnotic) responses from the purposeful escape movement (analgesic) responses to painful stimuli. The results indicated that adenosine compounds can selectively inhibit the pain and hemodynamic responses. Moreover, the experimental technique allows the testing of the efficacy and safety of anesthetic agents. This methodology can be used to screen an adenosine compound to determine if it can be used according to the method of the invention. The use of adenosine compounds without being carefully titrated or without proper cardiovascular monitoring can result in dangerous, life-threatening conditions to the subject or patient. It has now been established through, experimental and clinical testing that the effects of adenosine as anesthetic, analgesic, sedative, hypothermic, and stress inhibitor are predictable and dose dependent. These results indicate that the use of adenosine compounds is safe for humans and that the dosage can be selected by the clinician administering the drug. Effective dosages of adenosine compounds can be readily determined by monitoring the effect of a given dose on the blood pressure, heart rate, and arterial blood gases, as described herein.

Adenosine is known to have a short plasma half life. In order to achieve the process of this invention safely, a continuous infusion of adenosine or an adenine nucleotide can be used. An infusion of approximately 1 to 5500 µg of adenosine/kg body weight/min (hereinafter µg/kg/min), more preferably, 5 to 1000 µg/kg/min, even more preferably between 50 to 500 µg/kg/min, provides the effect of the invention.

The anesthetic effects of this invention are compared to standard inhalational anesthetic effects in terms of dose reduction in minimum alveolar concentration (MAC) of the inhaled anesthetics. MAC represents an index of anesthetic potency for comparison between different inhalational anesthetic drugs. After inhalation, only relatively small amounts of anesthetic gas is absorbed before the gas is exhaled. Therefore, those skilled in the art of anesthesiology define one MAC of a gaseous anesthetic at 1 atmosphere of pressure (760 torrs) as that amount which produces immobility in 50% of patients or animals exposed to painful stimulus. The use of MAC provides a convenient means of comparing the effect of the standard gaseous anesthetic agents, halothane, enflurane, methoxyflurane, isoflurane, and nitrous oxide to the anesthetic effect of the adenosine compounds.

The anesthetic and analgesic properties of the adenosine compounds are more easily compared to the effective dose of opioid analgesics. There, a dosage of opioid sufficient to produce immobility in 50% of patients or animals exposed to painful stimuli is defined as-the effective dose (hereinafter, ED50).

Referring to TABLE 1, various anesthetics and anesthetic agents are compared for efficacy (1) in producing sleep, (2) inducing analgesia, (3) reducing surgical stress, and (4) relaxing muscles. These are the four effects that anesthesiologists try to achieve during a surgical procedure. The chart confirms that no presently used agent is effective for all four effects. All known agents for stress relief are not included in the chart because most of these agents are normally considered to be cardiovascular medications, given primarily to treat cardiovascular disease, rather than anesthetic agents.

TABLE 1

| Component of Anesthesia | CHEMICAL AGENT | | | | | | |
|---|---|---|---|---|---|---|---|
| | Halothane Enflurane isoflurane | Nitrous Oxide | Barbiturates | Neuroleptics, Tranquilizers | Opioids | Muscle Relaxants | Adenosine Compounds |
| Sleep (unconsciousness, amnesia, sedation) | 3 | 1 | 3 | 2 | 2 | 0 | 2 |
| Antinociception (analgesia, less pain perception) | 1 | 1 | 1 | 1 | 3 | 0 | 3 |
| Inhibition of Stress (autonomic responses: blood pressure, heart rate; endocrine and metabolic responses) | 1 | 1 | 1 | 1 | 1 | 0 | 3 |
| Muscle Relaxation | 1 | 0 | 1 | 1 | 0 | 3 | 1 |
| TOTALS | 6 | 3 | 6 | 5 | 6 | 3 | 9 |

Anesthesia Score: 0 no effect; 1 minimal; 2 mostly; 3 maximal

In TABLE 1, a class of agents is rated for each of the four effects and graded on a scale of 0, indicating no effect, to 3, indicating a large effect. It can be seen that sleep is best sustained by the inhalation agents (e.g., halothane, and the like) and induced by barbiturates (e.g., sodium pentothal, and the like). Pain is most effectively relieved by the opioid analgesics (e.g., morphine, fentanyl, and the like). Muscle relaxation is typically induced by a paralytic agent (e.g., pancuronium, succinyicholine chloride, and the like). Each agent has two or more points of poor effectiveness, as shown by a 0 or 1 on the chart. As a result, in a surgical procedure, an anesthesiologist must use several different agents to achieve successful anesthesia. In particular, no currently used anesthetic agent has much effectiveness against the stress induced by surgery.

Adenosine compounds, on the other hand, are seen to provide excellent analgesia and stress relief, good sedation induction and maintenance, and fair muscle relaxation. Adenosine compounds work synergistically with other drugs thereby potentiating their properties. It should be understood that the adenosine compound can be administered in combination with other drugs at the discretion of the practitioner. Consequently, the dose of adenosine administered in a given situation may vary considerably depending on the presence of one or more other anesthetic agents. Determination of the appropriate dose in a particular instance is empirically ascertained by the practitioner using standard medical techniques known in the art.

An anesthetic procedure for surgery combines several effects. It provides pain relief, sedation, and sleep, and induces muscle relaxation. Typically, an anesthesiologist must relieve pain by an opioid or other analgesic, induce sleep by sodium pentothal or similar hypnotic, sustain sleep by an inhalational anesthetic, and relax muscles by the use of succinyl choline chloride or the like.

The method of the invention teaches the use of an adenosine compound to induce sedation, maintain sleep, reduce stress of surgery, and relieve pain while maintaining the circulatory and respiratory functions within normal ranges. In addition, the adenosine compound can induce hypothermia, rewarming (i.e., a return to normal body temperature), and maintain tissue perfusion and oxygenation. Therefore, by using the adenosine compounds according to the method of the invention, the adenosine compound comes closer to being an ideal anesthetic for surgical use and an effective drug for relief of pain, to induce sedation, and reduce stress.

Using the method of the invention, the adenosine compound may be the only agent required for certain uses, such as relief of chronic pain, or minor surgery where deep sleep is not necessary, but pain relief is a factor. Major surgery may require the additional use of some inhalational or intravenous anesthetics and some muscle relaxant.

When the analgesic effects of adenosine compounds, such as adenosine and ATP, were compared with the opioid compound, morphine sulfate, it was found that the adenosine compound was more potent without showing ceiling effect or respiratory depression observed by narcotics. The effective dosage range is an infusion from about 1 µg/kg/min to about 1000 µg/kg/min, preferably from about 50 µg/kg/min to about 500 µg/kg/min.

The adenosine compounds, adenosine and ATP, have been found to inhibit the CNS and the cardiovascular stress responses. They inhibit catecholamine release, hypertension, and vasoconstriction. They improve the cardiac function by after lead reduction when used as adjuvants to conventional anesthetics or hypnotic drugs. Furthermore, administration of the adenosine compound does not produce tachyphylaxis or depress cardio-respiratory function. The effective dosage range is an infusion from about 5 µg/kg/min to about 3000 µg/kg/min, preferably from about 20 µg/kg/min to about 600 µg/kg/min.

The anesthetic effects of an adenosine compound are determined by reducing the minimum alveolar concentration (MAC) of the inhaled anesthetics. For example, reducing enflurane MAC while administering an adenosine compound to achieve similar anesthesia or equipotent anesthesia. This process is done stepwise until total replacement of one inhalation agent is made, and while still achieving equipotent anesthesia. The effective dosage range is an infusion from about 5 µg/kg/min to about 1500 µg/kg/min, more preferably from about 30 µg/kg/min to about 500 µg/kg/min.

The sedative effects of adenosine compounds were observed by administering continuous infusions from about 1 µ/kg/min to about 1000 µg/kg/min. However, in the presence of noxious stimuli, the effective dosage was from about 5 µg/kg/min to about 1500 µ/kg/min, the preferred dosage being from about 5 µ/kg/min to about 500 µg/kg/min.

The tissue oxygenation effect was determined by measuring the oxygen pressure of vital organs such as the heart, brain, liver, kidney, and muscle tissues. Polarographic oxygen electrodes are used to monitor and measure the oxygen pressure of the tissue, and they were compared between different methods during severe stressful conditions such as hypotension. The effective dosage of adenosine compound is from about 5 µg/kg/min to about 2000 µg/kg/min.

The hypothermic and rewarming effects of an adenosine compound are tested in experimental animals prepared similarly as in the rabbit model described herein to test for anesthetic effects, except that the body temperature is allowed to fall. In animal studies (rabbit) where the room has a temperature of approximately 22° C., the body temperature will fall from a norm of about 39° C to about 32° C. in about three hours. If the animal is cooled further with ice bags, a temperature of approximately 22° C. can be achieved in three hours without cardiovascular decompensation. Rewarming is done with the aid of a thermal blanket and heat lamp. The effective dosages of adenosine compound ranged from about 100 µg/kg/min to about 5000 µg/kg/min.

The dosage ranges for the ,administration of the adenosine compounds according to the method of the invention are those large enough to produce the desired effect in which the desired physiologic state (e.g.,, anesthesia) is attained. The dosage should not be so large as to cause adverse side effects, such as hypotension, and the like. Generally, the dosage will vary with the age, condition, sex, and extent of the disease in the patient and can be determined by one of skill in the art. The dosage can be adjusted by the individual physician in the event of any counterindications.

The adenosine compounds can be administered parenterally by injection or by gradual perfusion or infusion over time. The adenosine compounds can be administered parenterally by such mutes as intravascularly, intrathecally, epidurally, intrapertitoneally, intramuscularly, subcutaneously, intracavity, transdermally, epidermally, nasopharyngeally, or mucosally. Alternatively, the adenosine compounds can be administered enterally, as by oral administration.

In contrast to other conventional anesthetics, the adenosine compounds are useful over a wide dose range. For example, adenosine is active over a range of between 1 to 5000 µg/kg/min. In contrast, conventional anesthetic agents, such as isoflurane, have narrow effective ranges. The fatal to effective anesthetic ratio of isoflurane is 3.02±0.13. Other reports indicate that isoflurane has about 1.88 times the safety range of halothane. When these ranges are stated simplistically, they suggest that if a patient is administered between two and five times the dose required for the onset of sleep, the patient will die. Of course, the anesthesiologist will err on the side of administering too little and, thereby, runs the risk of underdosing the patient. This need for caution may result in an inadequately anesthetized (subanesthetized) patient during the surgical procedure.

One great advantage observed with adenosine compounds is the wide margin for error on effective therapeutic range. This advantage is exemplified by adenosine where the lethal dose is about 100 times the dose required for analgesia, and ATP where the lethal dose is greater than 150 times the amount required for analgesia. In fact, in the case of ATP, the ratio remains unknown in the studies reported herein,. since no experimental animals died even when given enormous overdoses.

Formulations

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Liquid dosage forms for oral administration will generally comprise the adenosine compounds alone or in a composition additionally containing insipients such as emulsions, suspension, solutions, syrups, and elixirs containing inert diluents commonly used in the art, such as purified water, sugars, polysaccharides, silicate gels, gelatin, or an alcohol. In addition to the inert diluents, these compositions can also include factors such as wetting agents, emulsifying and suspending agents, and sweetening, flavoring, and perfuming agents.

The above disclosure generally describes the present invention. A more complete understanding can be obtained by reference to the following specific examples which are provided herein for purposes of illustration only and are not intended to limit the scope of the invention.

EXAMPLE 1

SCREENING OF ADENOSINE COMPOUNDS

This study describes a methodology which can be used to screen and identify adenosine compounds which can be used according to the method of the invention. A screening test to evaluate the therapeutic use of adenosine compounds ideally includes such parameters as: (1) noxious stimuli (e.g., tail clamp, electrical stimulation); (2) respiratory parameters (e.g., respiratory rate); (3) arterial blood gases (e.g., $PaCO_2$, $PaO_2$); (4) metabolic parameters (e.g., pH, BE); and (5) circulatory parameters (e.g., SBP, DBP, MBP, heart rate).

Anesthetic agents were assessed by using the electrical tail stimulation in the rabbit. The use of electrical stimulation as a way to produce noxious stimuli is an alternative to tail-clamping. It offers a method of applying noxious stimuli gradually in a quantifiable manner. By changing the intensity, two distinct behavioral responses are noted: (a) head lift (HL), an arousal response shown by opening the eyes and lifting the head (hypnotic index); and (b) purposeful escape movement (EM) away from the noxious stimuli (analgesic index). The responses in threshold voltages can be plotted on one axis, and the dosages can be plotted in the other axis.

In evaluating the adenosine compounds, unmedicated, healthy adult New Zealand white rabbits of either sex, weighing 4–5 kg were studied. The rabbits were first anesthetized by halothane 3–4% in oxygen via a circle system. Lidocaine 1% supplemented the halothane anesthesia when tracheostomy was performed and a 3.5 cuffed pediatric endotracheal tube was inserted into the trachea. The halothane concentration was then reduced to 2% in oxygen during the rest of the preparation period and no muscle paralyzing drug or an opioid analgesic was used at all. All animals were allowed to breathe spontaneously throughout the study. Expired halothane and carbon dioxide concentrations were monitored continuously using a Datex Anesthetic Agent Monitor 222 (Puritan-Bennett) and a capnometer (Beckman), respectively. Two ear veins and an ear central artery were cannulated with 22 gauge plastic catheters for drug infusion, and for blood sampling. The femoral artery and vein were cannulated and the catheters were placed with its tip in the mid-thoracic aorta to measure central arterial and venous blood pressures. Rectal temperature was controlled at 38.5°–39.5° C. with the aid of a heating lamp. All drugs were completely discontinued, and recovery was awaited.

The conscious rabbits were placed in a hammock which was suspended from four poles via ropes in such a manner that allowed each animal's neck, head, and legs to be free to move (for a clear response to the noxious stimuli). After complete recovery from the halothane anesthesia, control values were measured and recorded. Next, a gas mixture of nitrous oxide (60%) and oxygen (40%) was breathed through the endotracheal tube to maintain a baseline sedation. A pair of stimulating needle electrodes were placed at the base of the shaved tail, and electrical current was delivered for 40–60 seconds from a nerve stimulator (Grass S48 Stimulator) delivering rectangular pulses of current (1 ms, 3–5 Hz) with different intensities (1–80 V) for each test. Each infusion dose was maintained for 20 minutes.

No muscle paralyzing drug or mechanical ventilatory assistance was used through the experiments. Noxious stimuli were applied after each drug dose and maintained stable for 20 min. Neurobehaviorar responses, including degree of sedation, sleep, arousal responses (eye opening and head lifting), and antinociceptive responses (purposeful escape movement), were carefully observed and recorded by someone who was unaware of the agent being tested. Also, respiratory and circulatory parameters were measured and recorded: Systolic Blood Pressure (SBP), Diastolic Blood Pressure (DBP), Mean Arterial Blood Pressure (MAP), Respiratory Rate (RR), EKG, Body Temperature (BT). For the blood gases: pH, $PCO_2$, $PO_2$, $HCO_3$, BE.

Evaluation of (a) inhalation anesthetic (Halothane) (n=6), (b) intravenous analgesic (fentanyl) (n=5), and (c) adenosine (n=6) is shown in FIG. 1. The threshold responses for each drug were consistent and displayed typical characteristic profiles. Increasing doses of halothane consistently elevated the HL (hypnotic) and EM (analgesic) responses in a dose-dependent manner, whereas fentanyl and adenosine elevated EM responses, but the HL responses remained low, indicating analgesic properties. Adenosine effectively blocked the hemodynamic responses to noxious stimulation and maintained normal respiratory and blood gas parameters. On the other hand, fentanyl depressed ventilation as the doses were increased. Continuous infusion of adenosine for prolonged times did not cause drug accumulation or respiratory depression; these unique pharmacological qualities of adenosine are desirable features in clinical anesthesia. Based on the animal behavioral and hemodynamic responses to noxious stimuli, adenosine may be categorized as a rapid acting anesthetic with primarily analgesic properties. Using the methodology and screening test, evaluation of safety and efficacy of other adenosine compounds as anesthetics can be accomplished routinely without undue experimentation.

EXAMPLE 2

In this Example, ATP was substituted for enflurane (ENF), a standard inhalational anesthetic used clinically. The circulatory and respiratory effect of ATP and ENF were also compared. High doses of ENF with $N_2O$ attenuates responses to noxious stimuli, but causes cardio-respiratory depression. On the other hand, ATP provided sufficient anesthesia while avoiding cardio-respiratory depression.

Six intubated rabbits (4–5 Kg) spontaneously breathing 60% $N_2O$ in $O_2$ were studied. ENF concentrations of 0.5, 1.0, 1.5, 2.0, and 2.5% were added to $N_2O$ stepwise. After equilibration of each increased ENF dose, electrical tail stimulation (1 ms, 5 Hz) in increasing (graded) intensities as tolerated up to 80 V was applied. This kind of stimulation allowed quantifiable, and reproducible stimulation. Responses and measurements were taken every 20 minutes. In addition to the electrical stimulation, the tail clamping technique, a standard method of testing anesthetic potency, was used in order to establish the surgical level of depth of anesthesia. Furthermore, the ear and leg were clamped with a hemostat, and pin prick with a needle was applied to reconfirm nociceptive responses. Purposeful escape movements were used as end-points. When negative response to stimuli was achieved, the dose of ENF was decreased stepwise by 0.5% until positive response was shown; then, ATP infusion was titrated to replace the decreased ENF anesthesia until ATP could totally and effectively replace ENF (ATP initial dose: 5 µg/kg/min).

Figure 2:
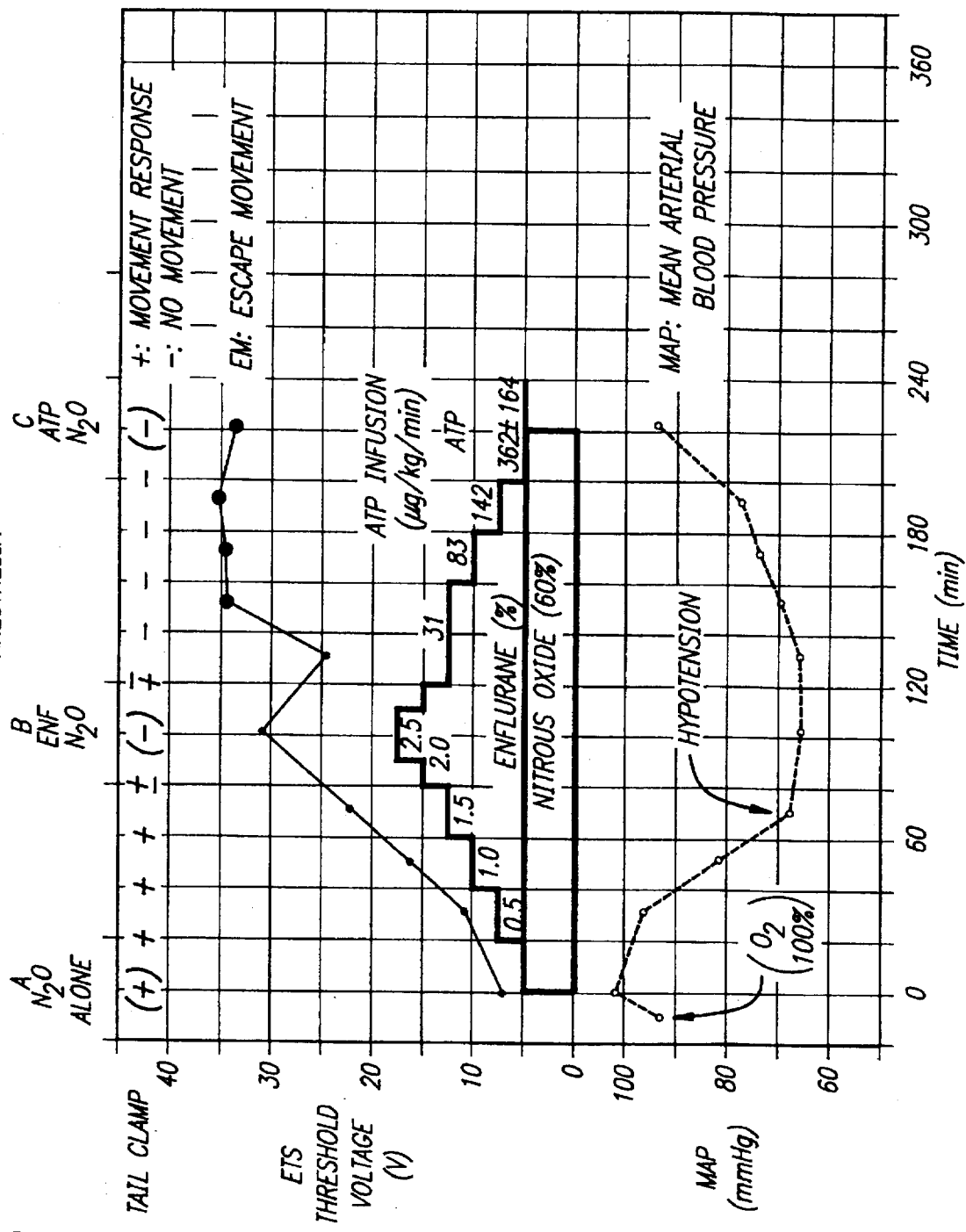
FIG. 2 illustrates the amount of anesthetic effect of ATP, measured as enflurane MAC.

Referring to FIG. 2, animals under 60% $N_2O$ and increasing doses of ENF up to 1.5% showed an elevated pain threshold, but still responded positively to the tail clamp. ENF, at levels greater than 2–2.5%, could completely inhibit such responses. At this dose, however, significant cardio-respiratory depression was seen (see TABLE 2). Addition of increasing doses of ATP (5–362 µg/kg/min) allowed ENF to be replaced without diminishing the pain tolerance. Moreover, systemic blood pressure (SBP) and heart rate (HR) returned to control levels, but analgesia persisted. Although adenosine and ATP have extremely short plasma half lives, IV ATP may have intrinsic analgesic activity in the CNS, since the selective analgesic effect persisted after the infusion had stopped. This effect may have been due to activation of central purinergic receptor mechanism which, once activated, has a long duration. This was seen by the observation of sustained analgesia after discontinuation of ATP which was partially reversed by IV aminophylline. This sustained analgesic property without cardio-respiratory depression may have marked clinical significance. These results demonstrated that the anesthetic effects of ATP were superior to enflurane as seen by the response of the cardiovascular parameters which were evaluated.

TABLE 2

CARDIO-RESPIRATORY DATA

|  | $O_2$ ONLY | CONTROL ($N_2O$) | ENF ($N_2O$) | ATP ($N_2O$) |
|---|---|---|---|---|
| SBP(mmHg) | 109 ± 11 | 126 ± 15 | 69 ± 22* | 112 ± 20 |
| DBP(mmHg) | 83 ± 5 | 85 ± 4 | 49 ± 18* | 83 ± 16 |
| HR(bpm) | 270 ± 13 | 267 ± 15 | 255 ± 33* | 278 ± 26 |
| RR(bpm) | 76 ± 5 | 85 ± 5 | 72 ± 19* | 81 ± 14 |
| PaCO$_2$(mmHg) | 25 ± 4 | 22 ± 2 | 25 ± 1* | 22 ± 3 |
| PaO$_2$(mmHg) | 443 ± 68 | 147 ± 11 | 148 ± 16 | 145 ± 24 |

RR: Respiratory Rate, $O_2$: 100%, $N_2O$: 60%, ENF: 2.0–2.5%, ATP: 32 ± 164 (µg/kg/min), Mean ± SD
*p < 0.05 vs CONTROL · (n = 6)

EXAMPLE 3

In this Example, the analgesic activity, the dose requirement, and the potency ratio of adenosine and morphine sulfate are compared.

The evaluation used six intubated rabbits (4–5 Kg) spontaneously breathing 60% $N_2O$ in $O_2$. Two forms of noxious stimuli were evaluated: (1) clamping the tail and the ear with a rubber-shod hemostat, and (2) electrical impulsing in increasing intensity, as tolerated, to a maximum of 80 v. This allows quantifiable, reproducible stimulation. Responses assessed were: HR, SBP, respiratory rate (RR), neurobehavior, and purposeful escape movements. After 20 min of 60% $N_2O$, control responses to stimulation were recorded. Adenosine was infused peripherally at increasing dosage until significant alterations in response to stimulation occurred. Normotension was maintained without pressure support. Duration and intensity of analgesia was evaluated every 15 min after termination of infusion. Aminophylline was given to reverse analgesic effects. Morphine sulfate was then titrated IV to max 2 mg/kg to attain a surgical level of analgesia (ED50 evaluated by the tail clamp response). No further doses were given if severe respiratory depression occurred.

Figures 3, 8:
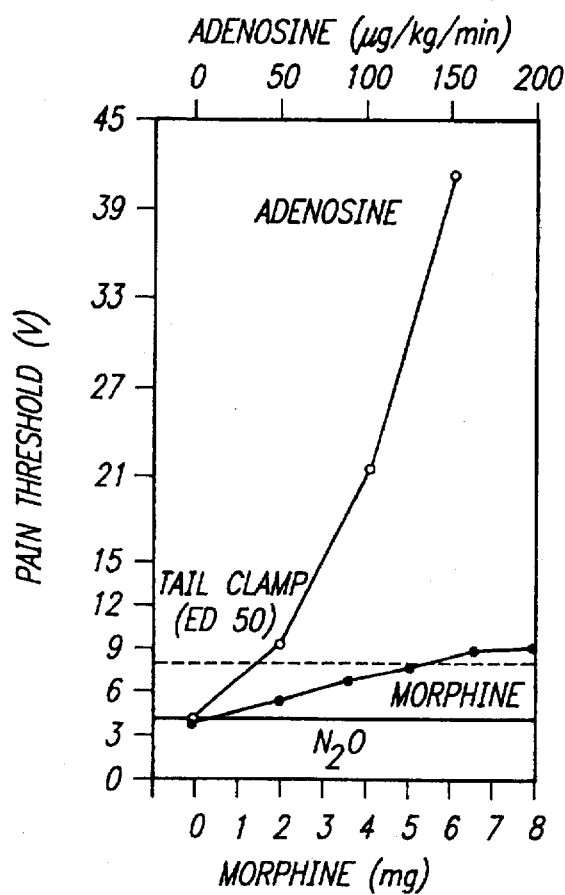
FIG. 3 shows the analgesic effect seen with morphine sulfate and adenosine.
FIG. 8 shows the anesthetic effects of ATP in terms of MAC in surgical patients.

Despite inhalation of 60% $N_2O$, all animals responded with purposeful escape movements to tail and ear clamp, and electrical stimulation. Addition of adenosine in doses of 188±20 µg/kg/min completely suppressed the responses to both kinds of stimulation (ED90). No motor or cardio-respiratory depression occurred, and no ceiling effect was noted. Aminophylline (5–10 mg/kg) consistently reversed adenosine induced analgesia: With morphine sulfate to 2 mg/kg, no animal had complete suppression of all responses. Referring to FIG. 3, a comparison of the effective analgesia of morphine sulfate and adenosine is shown. The effect of morphine sulfate appears to approach an asymptotic limit, thereafter giving no greater relief from pain (as measured by the voltage (v) of an electric stimulation), whereas adenosine provides more and more relief from pain.

TABLE 3

CARDIO-RESPIRATORY DATA

|  | CONTROL | ADENOSINE | MORPHINE |
|---|---|---|---|
| BP(mmHg) | 97 ± 12 | 101 ± 19 | 105 ± 14 |
| HR(bpm) | 240 ± 30 | 230 ± 24 | 242 ± 72 |
| RR(bpm) | 89 ± 10 | 85 ± 19 | 47 ± 16* |
| PaO$_2$(mmHg) | 136 ± 15 | 126 ± 8 | 123 ± 14 |
| PaCO$_2$(mmHg) | 22 ± 4 | 25 ± 4 | 31 ± 3* | n = 6, Mean ± SD, BP: Systolic BP, RR: Respiratory Rate,
*p < 0.05 vs CONTROL

This study demonstrates that adenosine, in sub-hypotensive doses, significantly raised thresholds for pain. Prolonged analgesia may be mediated by the adenosine $A_1$ receptor mechanism as supported by reversal of analgesia with aminophylline. Adenosine appears to have an analgesic potency ratio of about 25:1 as compared to morphine sulfate. Adenosine's property of sustained intense analgesia, absent cardio-respiratory depression, absence of "ceiling" effect, and easy reversibility provides excellent characteristics for its use in clinical anesthesia.

Figure 4:
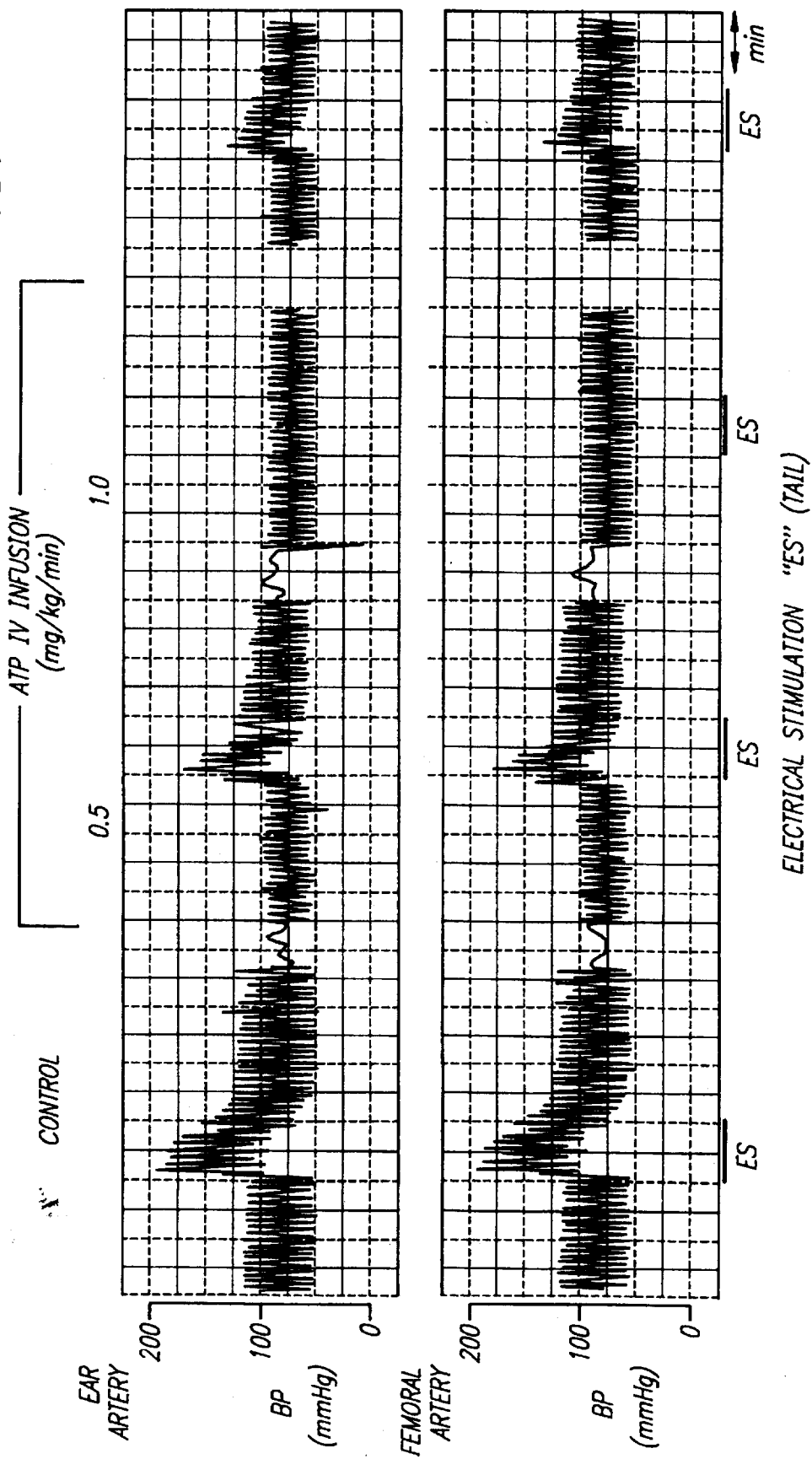
FIG. 4 shows the inhibition of stress response in blood pressure to the nociceptive electrical stimulation.
Figure 5:
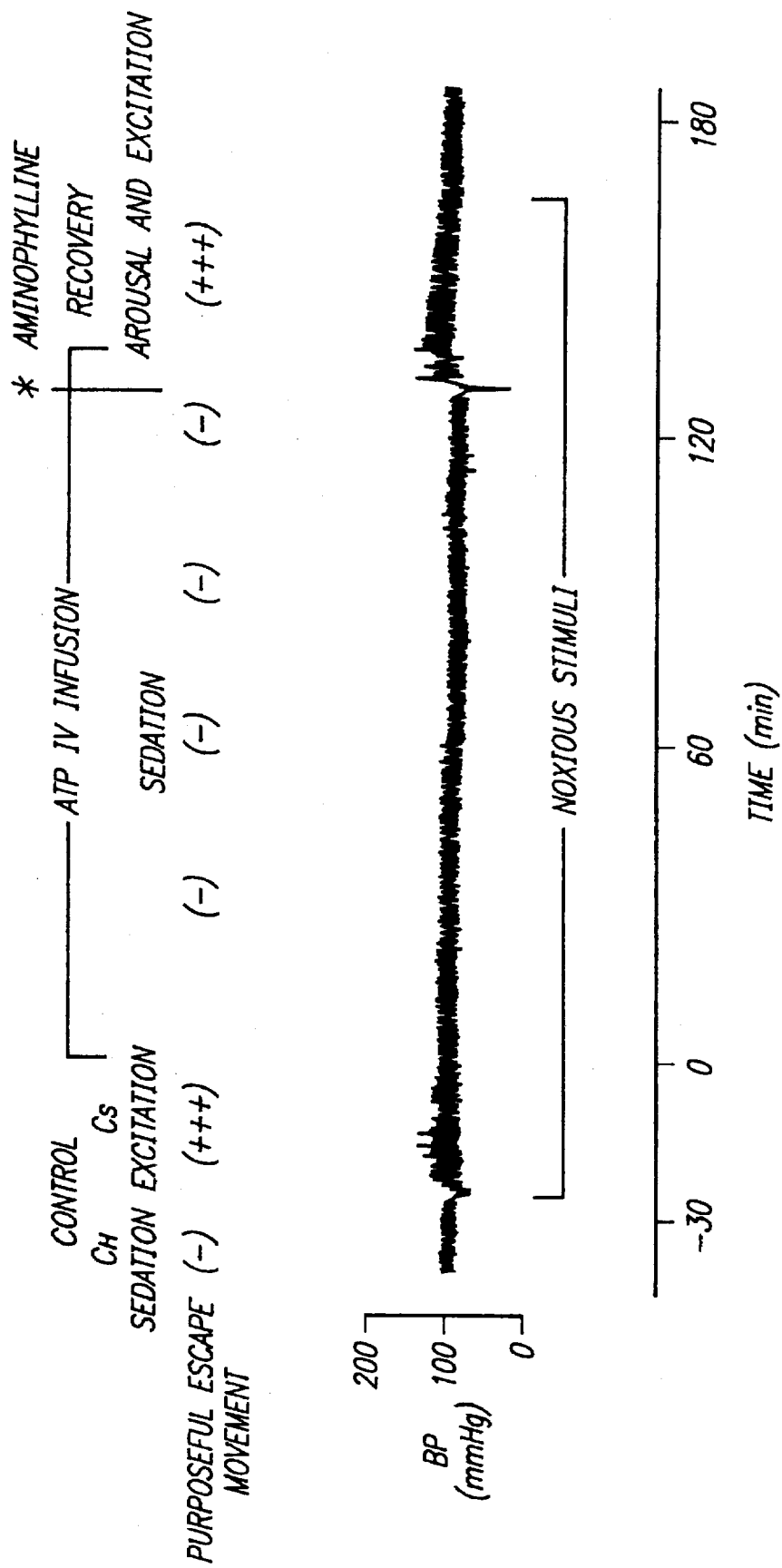
FIG. 5 shows the blood pressure responses and the sedative and analgesic effects of ATP for prolonged time.

As illustrated in FIG. 4, the blood pressure was recorded as described in Examples 2 and 3 as electrical stimulation was applied to the tail. When ATP was administered, purposeful escape movements decreased. When sufficient ATP was infused, no further purposeful escape movements or stress were seen as reflected by the blood pressure. FIG. 5 shows the blood pressure recording of the stable hemodynamic state obtained when ATP was administered during noxious stimulation for a prolonged time.

EXAMPLE 4

This Example shows a comparison of oxygen transport and regional tissue oxygenation during induced stress response caused by hypotension by hemorrhage, isoflurane, and adenosine triphosphate in dogs. These studies support the use of an adenosine compound in the in vivo preservation of a donor organ both in the donor mammal and in the recipient mammal after transplant, since the induced stress response mimics the condition existing in such circumstances.

The term "preservatively effective amount" refers to the concentration of adenosine compounds which is necessary to show as improvement in the preservation of a donor organ.

One of the most important concerns during hypotension is the fear of impaired vital organ perfusion and oxygenation. This study compared the changes in oxygen transport parameters and regional tissue oxygen tension of the parenchymal and non-parenchymal organ/tissues during graded arterial hypotension.

Twenty-three dogs (23.1±5 kg) were anesthetized with pentobarbital (30 mg/kg IV), intubated and mechanically ventilated with 40% $O_2$ in nitrogen to maintain normocapnea under normothermia (38° C.). Arterial and pulmonary artery (Swan-Ganz) catheters were placed via a femoral cut down. A Clark-type polarographic $PO_2$ electrode with a tip diameter (3 mm) was inserted under the dura and placed on the frontal cortex through a small burr hole.

Another $PO_2$ sensor probe was placed on the surface of the liver, kidney, subcutaneous, and muscle of the chest wall through a small skin incision. Referring to FIG. 6, the dogs were divided into three groups: (a) hemorrhagic (n=7), (b) isoflurane (n=8), and (c) ATP (n=8). Mean arterial pressure (MAP) was lowered stepwise from control (119±4.5 mmHg) to 90, 70, 50, and then to 30 mmHg, each being maintained for 20 minutes. The following were measured and/or calculated: MAP, $O_2$ consumption ($VO_2$), $O_2$ delivery ($DO_2$) and $PO_2$ of arterial ($PaO_2$) and mixed venous ($PvO_2$) of the brain ($PbO_2$), liver ($PlO_2$), kidney ($PkO_2$), subcutaneous ($PscO_2$), and muscle ($PmO_2$) of the chest wall. The data were analyzed using ANOVA with the Bonferroni t-test and unpaired t-test where appropriate, accepting p<0.05 as significant.

Figures 6A, 6B, 6C:
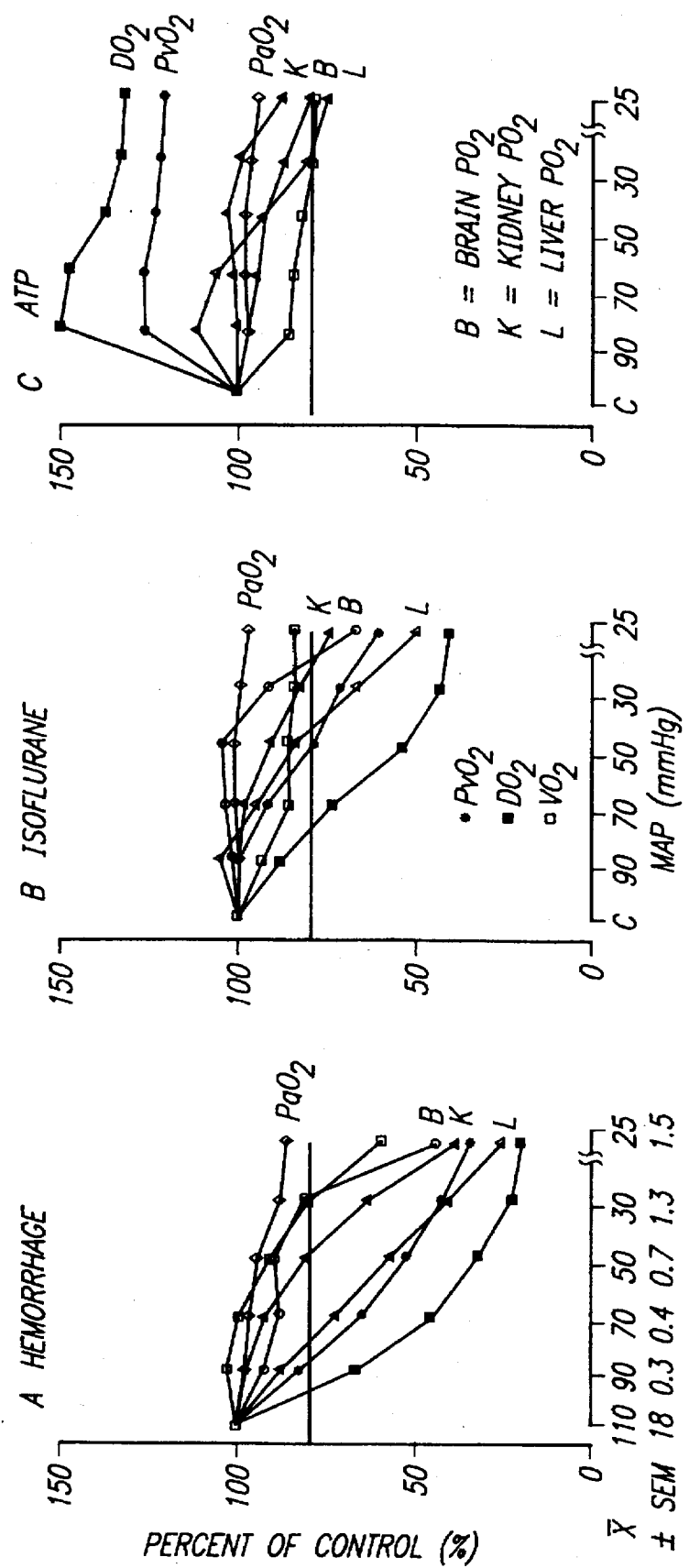
FIG. 6a shows the effect of hemorrhage.
FIG. 6b shows the effect of isoflurane.
FIG. 6c shows the effect of ATP.

Results are illustrated in FIGS. 6a, 6b, and 6c. During the sequential hypotension, $PaO_2$ remained unchanged. Due to autoregulation, cerebral cortical $PbO_2$ was little affected in all groups. However, there were markedly different hemodynamic and tissue oxygen responses between the three different hypotensions. Hemorrhage caused intense peripheral vasoconstriction. Isoflurane blunted these peripheral vasoconstrictive responses. However, with higher dosage isoflurane seriously depressed $DO_2$ resulting in a reduced $O_2$ supply/demand ratio, while ATP maintained better balanced $O_2$ transport profile which resulted in a positive $O_2$ supply/demand ratio in all stages of hypotension favoring the tissue oxygenation preferentially to the vital organs.

EXAMPLE 5

This Example shows the effects of adenosine and adenosine triphosphate on hypothermia in rabbits. As used herein, the term "hypothermally effective amount" denotes that concentration of adenosine compounds which is needed to induce hypothermia, i.e., a subnormal body temperature.

Figure 7:
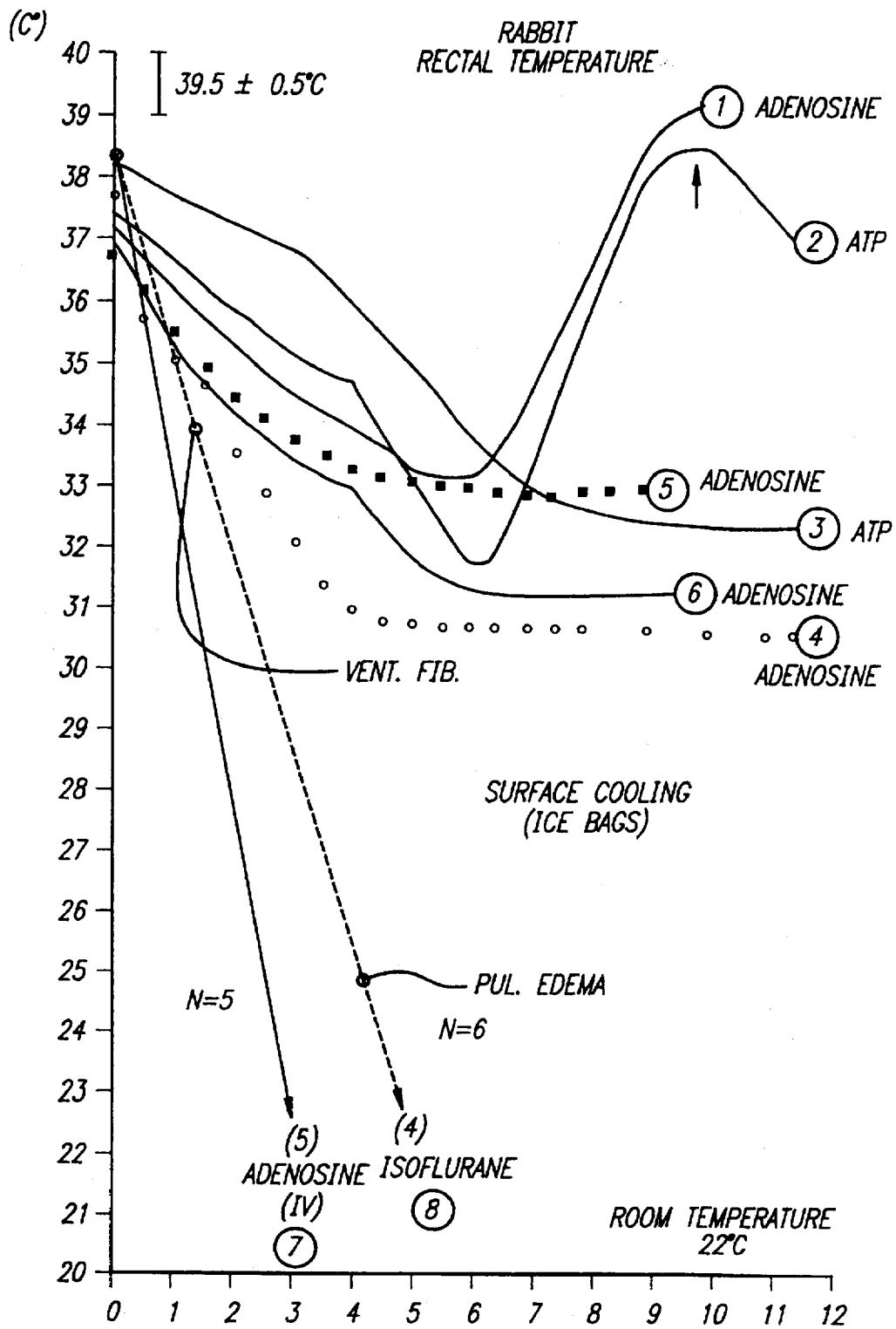
FIG. 7 illustrates the relationship between body temperature and time for various doses of adenosine and ATP.

Referring to FIG. 7, the body temperature versus time plots are shown for eight different experiments. In Run 1, adenosine 500 µg/kg/min was administered intravenously to rabbits for six hours. The administration was then stopped and the body temperatures were allowed to recover.

In Run 2, ATP 500 µg/kg/min was administered intravenously for six At that time, the body temperature was 31.5° C. The animal's body temperature was allowed to recover by applying external heating for four hours when (at the arrow) the external heating was removed and the temperature was allowed to fall. The body temperature again fell.

In Run 3, ATP was administered intravenously. The body temperature stabilized after ten hours at 32.5° C.

In Runs 4, 5, and 6, adenosine was administered to rabbits until the body temperature reached a constant value. In Run 4, after five hours, the body temperature stabilized at 33° C. In Run 6, after six hours, the temperature stabilized at 31.5° C.

In Run 7, five unmedicated New Zealand rabbits were anesthetized with halothane in $O_2$ using a face mask. The ear vein was cannulated with a 22 gauge plastic catheter for drug infusion. 500 µg/kg/min to 5500 µ/kg/min adenosine was administered IV. Body temperature was monitored through a rectal thermometer. The body temperature started at approximately 38.5° C. After the application of ice bags, the temperature dropped approximately 5.5° C./hr until a minimum body temperature of approximately 22° C. was achieved. During the body temperature lowering, no shivering or other apparent discomfort was observed. All five rabbits survived the temperature lowering.

The ice bags were removed and external heating applied. The body temperature of all rabbits returned to normal, and the rabbits were apparently normal.

In a comparison, in Run 8, six rabbits were anesthetized with isofluane and external cooling applied. At 34° C., one rabbit expired due to ventricular fibrillation. At 25° C., another expired due to pulmonary edema. All rabbits receiving isoflurane alone were observed to shiver violently as body temperature was lowered.

EXAMPLE 6

In this Example, intrathecal administration of adenosine was shown to be effective. Anesthesia was induced in unmedicated New Zealand white rabbits (4–5 Kg) with 3–4% halothane in oxygen using a face mask. The trachea was intubated with a No. 3.5 pediatric endotracheal tube. All the animals breathe spontaneously throughout the study, but were mechanically ventilated when required. Rectal temperatures were controlled at 38.5°–39.5° C. Expired halothane and carbon dioxide concentrations were monitored continuously. Two ear veins and an ear central artery were cannulated with 22 gauge plastic catheters for drug infusion and for blood gas monitoring. The groin was exposed and a cut-down performed on the femoral artery and vein. The femoral artery was cannulated and the catheter placed with its tip in the mid-thoracic aorta to measure central systemic blood pressures. Another central venous catheter was inserted through the femoral vein.

The animal was turned in a prone position and the operative site prepared over the lower back. The skin was infiltrated with 2% lidocaine 3–4 cc. Following dissection through the paravertebral muscles, a laminectomy was performed. A touhy needle was placed under direct vision into the sub-arachnoid space and a microcatheter (22–32 gauge) was threaded through the needle advancing it gently so that its tip was at the base of the skull. Clear CSF was aspirated to confirm sub-arachnoid placement. The laminectomy site was disinfected and sutured to close the site. The catheter was secured with tape.

Noxious stimulation was provided by an electrode placed at the base of the tail for low voltage electrical current stimulation delivered through a nerve stimulator. Other kinds of stimulations were in the form of a pin prick with a 20 gauge needle, pinching the paw and tail clamping with a rubber-shod hemostat.

Continuous recording of cardio-respiratory parameters including the heart rate, arterial blood pressure, respiratory rate, the animal's physical movement, and any other behavioral changes were recorded. Samples of arterial and mixed venous blood were analyzed for pulmonary gas exchange and acid base status.

Several intrathecal dosage forms were evaluated: lidocaine was given in 0.5 mg/kg increments; fentanyl was given in 1 μg/kg increments; adenosine was given as a fractionated dose, as well as via a continuous infusion (10 mg/hr) based on the body weight of the rabbit.

TABLE 4

CIRCULATORY AND RESPIRATORY CHANGES AFTER INTRATHECAL* INJECTION OF ADENOSINE, FENTANYL AND LIDOCAINE

| | ADENOSINE (20 mg) | FENTANYL (20 μg) | LIDOCAINE (4 mg) |
|---|---|---|---|
| Δ MAP (mmHg) | −4 ± 5 | +13 ± 5 | −65 ± 4 |
| Δ HR (bpm) | −22 ± 5 | −65 ± 33 | −25 ± 40 |
| Δ RR (bpm) | −4 ± 10 | −82 ± 15 | −140 ± 46 |
| Δ $PaCO_2$ (mmHg) | −6.8 ± 2.1 | +2.3 ± 2.5 | +10 ± 2 |
| Δ $PaO_2$ | +10 ± 14 | −11 ± 12 | −48 ± 10 |

MAP: Mean Arterial Pressure, HR: Heart Rate in beats per minute, RR: Respiratory Rate in breaths per minute. Mean ± SD
*Intrathecal injection in the high spinal (C1 area).

As shown in TABLE 4, comparison of the various drugs indicates that intrathecal administration of adenosine was as effective as intrathecal fentanyl in reducing the response to the noxious stimulation, but without the cardio-respiratory effects seen when fentanyl or lidocaine were used.

EXAMPLE 7

EFFECT OF ATP ANESTHESIA ON THE CARDIO-RESPIRATORY FUNCTIONS IN SURGICAL PATIENTS

High doses of volatile anesthetics or opioids are required to suppress autonomic and hemodynamic responses to surgical stimulation. The use of enflurane (ENF) for prolonged surgery may cause potential problems including severe cardio-respiratory depression, EEG abnormalities, and delayed awakening. This study compared the cardio-respiratory and plasma catecholamine changes during balanced anesthesia of $N_2O$-ATP-$O_2$ or ENF-ATP-$O_2$ with the conventional ENF-$N_2$-O-$O_2$ anesthesia in patients undergoing oral surgery.

Following institutional approval, 14 ASA-1 consenting patients were studied (FIG. 8). Patients were induced with IV thiopental (4–5 mg/kg), and endotracheal intubation was facilitated with succinylcholine (1 mg/kg). All patients were allowed to breathe spontaneously with manual assistance when needed throughout the procedure. No further muscle relaxant or opioid analgesic was used. Anesthesia was initially maintained by inhaling a gas mixture of enflurane and 60% nitrous oxide in oxygen via a circle anesthesia breathing system. Monitoring included continuous pulse oximeter, ECG (11), heart rate (HR), radial artery blood pressure (BP), urine output, inspired and expired anesthetic gases (ENF (enflurane), $N_2O$ (nitrous oxide), $O_2$, $CO_2$ (Datex. Capnomac)), arterial blood gases (Radiometer), plasma catecholamines (HPLC), and non-invasive esophageal ultrasound doppler probe (Datascope) for cardiac output (CO) and stroke volume (SV) measurements. ATP 2% solution (Adephos (R) Kowa) was infused into a peripheral vein via a continuous syringe infusion pump (Terumo) to support BP and HR within 20% from the pre-anesthetic levels.

The doses used for ATP (108±21 μg/kg/min) were much lower than those to induce deliberate hypotension. During surgery, anesthesia was maintained initially with 1.34 MAC ENF/$N_2O$/$O_2$ then doses of ENF or $N_2O$ were gradually decreased while ATP infusion was increased and titrated until either ENF or $N_2O$ was completely replaced by ATP. This resulted in new combinations of anesthesia: Group I: ATP/$N_2O$/$O_2$ (n=7), and Group II: ATP/ENF/$O_2$ (n=7).

Patient characteristics and the main results are shown in TABLES 5–7. Neurobehavioral and sympathetic responses (movement of body or arm, eye opening, nydriasis, tearing, sweating, and catecholamine levels) were carefully monitored by the anesthesiology team and, in addition, by an extra observer. Since patients were not paralyzed, any of the above signs would have been noticed if there were an inadequate level of anesthesia at any time during surgery. No patient had intraoperative event recollection, nightmares or other dreams, or any other unpleasant anesthetic experience. Furthermore, most patients experienced an unexpected sustained analgesia in the recovery room.

TABLE 5

HAEMODYNAMIC, RESPIRATORY AND PLASMA CATECHOLAMINE DATA DURING ENFLURANE/$N_2O$ AND ATP/$N_2O$ ANESTHESIA IN SURGICAL PATIENTS

| | ENFLURANE + NITROUS OXIDE | ATP + NITROUS OXIDE |
|---|---|---|
| Haemodynamic: | | |
| HR (beat/min) | 99 ± 16 | 95 ± 12 |
| SBP (mm/Hg) | 113 ± 21 | 129 ± 18 |
| MBP (mm/Hg) | 79 ± 22 | 78 ± 16 |
| DBP (mm/Hg) | 63 ± 18 | 54 ± 15 |
| CO (L/min) | 4.3 ± 1.6 | 6.7 ± 2.4* |
| SV (ml) | 44 ± 21 | 70 ± 23* |
| Respiratory: | | |
| RR (breath/min) | 16 ± 4 | 19 ± 3* |
| pH | 7.33 ± 0.04 | 7.34 ± 0.06 |
| $PaCO_2$ (mmHg) | 45 ± 4 | 39 ± 3* |
| $PaO_2$ (mmHg) | 202 ± 28 | 191 ± 57 |
| BE | −2.0 ± 2.0 | −2.4 ± 1.2 |
| Plasma Catecholamine: | | |
| NE (pg/ml) | 296 ± 166 | 429 ± 270* |
| EPI (pg/ml) | 92 ± 90 | 153 ± 76 |

Mean ± SD, *p < 0.05, $N_2O$: 60% in $O_2$, Enflurane: 1.33 ± 0.42%, ATP: 113 ± 19 μg/kg/min, CO: Cardiac Output, SV: Stroke Volume, RR: Respiratory Rate, N = 7.

TABLE 6

HAEMODYNAMIC, RESPIRATORY AND PLASMA CATECHOLAMINE DATA DURING $N_2O$/ENFLURANE AND ATP/ENFLURANE ANESTHESIA IN SURGICAL PATIENTS

|  | NITROUS OXIDE + ENFLURANE(a) | ATP + ENFLURANE(b) |
|---|---|---|
| Haemodynamic: | | |
| HR (beat/min) | 82 ± 11 | 97 ± 17 |
| SBP (mm/Hg) | 114 ± 14 | 100 ± 19 |
| MBP (mm/Hg) | 84 ± 15 | 61 ± 12* |
| DBP (mm/Hg) | 69 ± 14 | 44 ± 8* |
| CO (L/min) | 5.4 ± 2.5 | 10.5 ± 1.3* |
| SV (ml) | 65 ± 10 | 108 ± 23* |
| Respiratory: | | |
| RR (breath/min) | 19 ± 3 | 19 ± 2 |
| pH | 7.37 ± 0.02 | 7.35 ± 0.02 |
| $PaCO_2$ (mmHg) | 47 ± 7 | 44 ± 7* |
| $PaO_2$ (mmHg) | 215 ± 23 | 568 ± 50* |
| BE | −0.4 ± 0.9 | −0.5 ± 0.9 |
| Plasma Catecholamine: | | |
| NE (pg/ml) | 178 ± 102 | 351 ± 98* |
| EPI (pg/ml) | 86 ± 19 | 150 ± 130 |

Mean ± SD, * $p < 0.05$, $N_2O$: 60% in $O_2$, Enflurane(a): 1.24 ± 0.48%, Enflurane(b): 0.91 ± 0.12%, ATP: 103 ± 23 µg/kg/min, CO: Cardiac Output, SV: Stroke Volume, RR: Respiratory Rate, N = 7.

Besides sleep and analgesia, maintenance of respiratory and hemodynamic stability during surgery, is a major objective in anesthesia. Neither ENF or $N_2O$ alone can provide complete anesthesia, and even their combination is not entirely satisfactory. Replacement of either ENF of $N_2$ by intravenous ATP resulted in a better anesthetic state with improved cardio-respiratory effects. No ventilatory or blood gas deterioration was seen during ATP infusion in spontaneously breathing patients.

TABLE 7

PATIENT AND ANESTHESIA CHARACTERISTICS*

| 14 Patients: | 5 M and 9 F |
|---|---|
| Ages (years): | 27 ± 13 |
| Body Weight (Kg): | 57 ± 11 |
| Height (cm): | 167 ± 7 |
| Premedication (IM): | |
| Atropine: | 0.5 mg |
| Pentazocine: | 15 mg |
| Hydroxyzine: | 75–100 mg |
| Anesthesia time (min): | 273 ± 107 |
| Surgery time (min): | 202 ± 100 |
| ATP infusion time (min): | 67 ± 8 |
| ATP infusion dose: | 108 ± 21 (µg/kg/min) |
| Dipyridamole dose: | 0.2 mg/kg |
| Urine output (ml/h): | 111 ± 16 |

*Mean ± SD

The cardiac functions: cardiac output and stroke volume were ameliorated in both ATP groups, but the ATP/ENF/$O_2$ group showed a tendency of lower diastolic blood pressure than the ATP/$N_2O$/$O_2$ group. This may be due to the synergistic vasodilating effects of ENF and ATP. On the other hand, ATP seems to have compensated for the sympathetic mediated vasoconstriction of $N_2$. Therefore, ATP/$N_2O$/$O_2$ appears to be a more desirable combination.

EXAMPLE 8

USE OF ATP TO ATTENUATE STRESS RESPONSE IN HUMANS

This study examined the ability of ATP to suppress the surgical stress responses to surgery. A rapid induction and recovery from anesthesia without side effects are features largely sought by anesthesiologists and surgeons.

Following institutional approval, 34 consenting ASA-1 or 2 patients undergoing various kinds of surgical procedures, were divided in two groups: (A) Patients who did not require muscle relaxant and breathed spontaneously (n=20); and (B) Patients requiring muscle relaxants who were mechanically ventilated (n-14). After a standard dose of premedication (atropine 0.5 mg/kg. hydroxyzine 50–75 mg intramuscularly), anesthesia was induced with intravenous thiopental (5 mg/kg), and endotracheal intubation facilitated with succinylcholine (1 mg/kg). Following intubation, enflurane (ENF) and nitrous oxide ($N_2O$) anesthesia was initially maintained with inspired concentration of ENF (1.5–2.0%) and $N_2$ (67%) in oxygen ($O_2$). Anesthetic gases were delivered at a constant total fresh gas flow rate of 6 liters/min (4L $N_2O$+2L $O_2$) using an anesthesia machine (Ohmeda Modulus II, BOC) via circle $CO_2$ absorption breathing system with a 2-liter reservoir bag. In Group B, muscle relaxation was achieved with pancuronium bromide (0.03–0.05 mg/kg) as required, and the lungs were mechanically ventilated. At the end of the surgical procedure, residual muscle relaxation was antagonized by atropine sulfate (0.02 ng/kg) and neostigmine (0.04 mg/kg).

Monitoring included a precordial stethoscope, continuous electrocardiography (ECG), heart rate, brachial automatic noninvasive cuffed blood pressure monitor, pulse oximeter, hourly urine output, and inspired and expired anesthetic gas concentration as measured by a laser anesthetic gas analyzer (Rascal. Albion Instr.). Arterial blood gases/acid-base status were assessed with appropriate electrodes (AVL 940 Blood Gas Analyzer). ATP 2% solution (Adephos (R) Kowa) was administered intravenously via a peripheral arm vein using a continuous syringe infusion pump (STC 521, Terumo) at infusion rates between 30–190 µg/kg/min to ensure adequate depth of anesthesia and hemodynamic stability. Thereafter, ATP doses and ENF concentrations were titrated to maintain blood pressure (BP) and heart rate (HR) within 20% from the pre-operative values, and low concentrations of ENF were administered and adjusted during surgery. Data are presented as mean and standard deviation (SD) or standard error of the mean (SEM) as appropriate. Significance was tested using paired or unpaired student's t-test were applicable. A P value of less than 0.05 was considered significant.

Patient and anesthesia data are shown in TABLES 8–10. In combination with $N_2O$ continuous infusion of ATP effectively inhibited cardiovascular as well as neurobehavioral responses to surgery. BP and HR were easily titrated (FIGS. 9–10) and stable hemodynamic, respiratory, and blood gas values were maintained in both groups. Intra-operative urine output was 58.7 (±43.3) ml/hr in Group A, and 71.8 (±44.6) ml/hr in Group B, respectively.

TABLE 8

PATIENT AND ANESTHESIA DATA: SPONTANEOUS VENTILATION (NO MUSCLE RELAXANT)

| Patient No. | Age Year | Sex | Body Weight (Kg) | Surgical Procedure | Anesthesia Time (min) | Surgery Time (min) | ATP Infusion Time (min) | ATP Dose (µg/kg/min) Min | Max |
|---|---|---|---|---|---|---|---|---|---|
| 1 | 55 | F | 47 | Tympanoplasty | 270 | 220 | 210 | 30 | 60 |
| 2 | 32 | F | 65 | Plastic Surgery (neck) | 125 | 80 | 90 | 50 | 70 |
| 3 | 53 | F | 60 | Reconstructive (face) | 175 | 115 | 135 | 50 | 80 |
| 4 | 42 | F | 62 | Mastectomy | 240 | 195 | 210 | 40 | 60 |
| 5 | 60 | M | 44 | Mandibular Fracture | 130 | 90 | 105 | 50 | 100 |
| 6 | 33 | F | 52 | Reconstructive (face) | 290 | 255 | 270 | 50 | 100 |
| 7 | 24 | F | 46 | Mandibular Surgery | 140 | 105 | 105 | 50 | 100 |
| 8 | 62 | F | 50 | Mastectomy | 165 | 105 | 120 | 50 | 100 |
| 9 | 53 | F | 57 | Bilateral Femur Fracture | 340 | 275 | 320 | 50 | 100 |
| 10 | 43 | F | 52 | Mastectomy | 180 | 105 | 130 | 50 | 100 |
| 11 | 22 | M | 60 | Reconstructive (face) | 220 | 180 | 155 | 50 | 120 |
| 12 | 14 | F | 51 | Low Back Tumor | 145 | 83 | 105 | 30 | 120 |
| 13 | 41 | F | 55 | Thyroidectomy | 160 | 105 | 120 | 40 | 110 |
| 14 | 15 | M | 55 | Tympanoplasty | 225 | 175 | 180 | 60 | 160 |
| 15 | 49 | F | 45 | Tympanoplasty | 220 | 167 | 170 | 60 | 110 |
| 16 | 17 | M | 68 | Mandibular Fracture | 230 | 187 | 160 | 50 | 140 |
| 17 | 33 | F | 43 | Parathyroidectomy | 160 | 120 | 105 | 70 | 110 |
| 18 | 48 | F | 46 | Tympanoplasty | 150 | 100 | 105 | 60 | 140 |
| 19 | 20 | F | 48 | Reconstructive (face) | 250 | 180 | 215 | 60 | 90 |
| 20 | 51 | M | 56 | Parathyroidectomy | 170 | 125 | 120 | 60 | 110 |
| Mean | 38.4 | | 53.1 | | 199.3 | 148.4 | 156.5 | 51.5 | 103.0 |
| (SD) | (15.6) | | (7.3) | | (58.5) | (58.0) | (61.7) | (10.9) | (27.2) |

TABLE 9

PATIENT AND ANESTHESIA DATA: CONTROLLED VENTILATION (MUSCLE RELAXANT)

| Patient No. | Age Year | Sex | Body Weight (Kg) | Surgical Procedure | Anesthesia Time (min) | Surgery Time (min) | ATP Infusion Time (min) | ATP Dose (µg/kg/min) Min | Max |
|---|---|---|---|---|---|---|---|---|---|
| 1 | 43 | F | 42 | Hysterectomy | 160 | 100 | 110 | 50 | 100 |
| 2 | 52 | F | 63 | Cholecystectomy | 315 | 260 | 250 | 60 | 160 |
| 3 | 71 | F | 41 | Liver Resection | 280 | 223 | 225 | 60 | 120 |
| 4 | 58 | M | 58 | Gastrectomy | 255 | 215 | 210 | 60 | 160 |
| 5 | 56 | F | 51 | Cholecystectomy | 115 | 55 | 60 | 60 | 110 |
| 6 | 41 | F | 41 | Hysterectomy | 145 | 102 | 105 | 60 | 80 |
| 7 | 46 | F | 51 | Hysterectomy | 115 | 80 | 70 | 60 | 110 |
| 8 | 53 | F | 46 | Cholecystectomy | 100 | 70 | 55 | 70 | 120 |
| 9 | 43 | F | 44 | Hysterectomy | 140 | 100 | 115 | 60 | 170 |
| 10 | 55 | F | 60 | Oophorectomy | 270 | 205 | 195 | 60 | 110 |
| 11 | 43 | F | 49 | Hysterectomy | 145 | 103 | 110 | 70 | 150 |
| 12 | 52 | F | 46 | Hysterectomy | 170 | 110 | 120 | 70 | 140 |
| 13 | 57 | F | 68 | Cholecystectomy | 130 | 85 | 95 | 70 | 160 |
| 14 | 59 | M | 60 | Sigmoidotomy and Cholecystectomy | 260 | 215 | 210 | 60 | 190 |
| Mean | 52.1 | | 51.4 | | 185.7 | 137.4 | 137.9 | 62.1 | 134.3 |
| (SD) | (8.3) | | (8.9) | | (73.3) | (69.2) | (66.0) | (5.8) | (31.6) |

TABLE 10

ARTERIAL BLOOD GAS DATA BEFORE AND DURING ATP INFUSION IN SPONTANEOUSLY (A) AND MECHANICALLY (B) BREATHING PATIENTS

| | Pre-ATP | ATP Infusion Time 60 min | 120 min | 180 min | 240 min |
|---|---|---|---|---|---|
| GROUP A | n = 17 | n = 18 | n = 16 | n = 3 | n = 1 |
| pH | 7.35 (0.06) | 7.33 (0.03) | 7.34 (0.03) | 7.36 (0.03) | 7.39 (0.0) |
| $PCO_2$ | 43.8 (10.4) | 44.1 (6.9) | 41.9 (6.6) | 39.9 (8.6) | 31.0 (0.0) |
| $PO_2$ | 156.4 (40.7) | 140.9 (38.9) | 137.9 (37.3) | 165.5 (24.6) | 115.1 (0.0) |
| BE | −2.3 (1.8) | −3.3 (1.9) | −3.2 (2.4) | −3.0 (1.8) | −4.1 (0.0) |
| Hb | 12.7 (1.7) | 12.6 (1.8) | 12.8 (1.8) | 11.9 (2.0) | 10.7 (0.0) |
| GROUP B | n = 14 | n = 14 | n = 10 | n = 5 | n = 4 |
| pH | 7.40 (0.05) | 7.34 (0.07)* | 7.33 (0.06)* | 7.32 (0.04)* | 7.288 (0.03)* |

TABLE 10-continued

ARTERIAL BLOOD GAS DATA BEFORE AND DURING ATP INFUSION IN
SPONTANEOUSLY (A) AND MECHANICALLY (B) BREATHING PATIENTS

|  | | ATP Infusion Time | | | |
|---|---|---|---|---|---|
|  | Pre-ATP | 60 min | 120 min | 180 min | 240 min |
| $PCO_2$ | 36.5 (6.3) | 40.2 (7.6) | 40.1 (7.2) | 41.6 (4.6) | 45.4 (3.6)* |
| $PO_2$ | 168.9 (25.7) | 140.3 (30.9)* | 142.6 (36.3)* | 130.4 (26.7)* | 130.1 (24.1)* |
| BE | −1.8 (1.3) | −4.2 (1.9)* | −4.8 (1.3)* | −5.2 (1.1)* | −5.4 (1.1)* |
| Hb | 11.9 (1.6) | 11.7 (1.8) | 11.2 (2.1) | 11.8 (1.9) | 11.7 (2.2) |

Mean(SD), *$p < 0.05$ vs Pre-ATP

Continuous infusion of ATP enabled the ENF requirement to be markedly reduced. ENF administration was completely discontinued approximately 30–60 minutes before surgery was concluded. No abnormal neurobehavioral sign of inadequate anesthesia (body or arm movement, coughing, mydriasis, tearing, sweating) was seen at any time during ATP infusion. After discontinuation of $N_2O$ and ATP, all patients emerged from anesthesia smoothly, and almost immediately, responsed and followed verbal commands such as opening their eyes, opening their mouth, squeezing "my hand". No agitation, grimacing, thrashing, and back-arching was seen despite the presence of the endotracheal tube. After gentle oro-laryngeal suctioning, patients were safely extubated. Post-anesthesia recovery was smooth without experiencing nausea, vomiting, or shivering. Within ten minutes after extubation, the patients were well oriented, clear-headed, and remained calm without any sign of respiratory depression. No patient complained of intraoperative awareness or unpleasant experience. Patients who had previous experience of general anesthesia felt that, in terms of postoperative well being, this was their anesthetic of choice for the future.

In addition to the hypnotic and analgesic state, rapid induction of anesthesia and maintenance of respiratory and hemodynamic stability during surgery have been major objectives in anesthesia. High doses of volatile anesthetics or opioids are required to suppress somatic, autonomic, and hemodynamic responses to surgical stimulation. However, the use of sufficient doses of either inhalation anesthetics or opioid analgesics, to inhibit intense and continuous surgical stimulation for prolonged surgical procedures, may cause severe cardio-respiratory depression, metabolic disturbances, EEG abnormalities, and delayed awakening from anesthesia which may take several hours or even days. Furthermore, emergence from anesthesia is often stormy and complicated with events such as persistent hypertension, hypotension, drowsiness, nausea, vomiting, airway obstruction, shivering, hypoxia, and the like.

In the present study, hemodynamic and respiratory functions were well maintained during ATP infusion. In contrast, erratic swings in BP and HR occurred during nitrous oxide, ENF anesthesia, and at surgical incision before ATP. A noteworthy post-operative course was characterized by absence of excitatory and stormy emergence. The most intriguing experience was to see the patients calm and tolerating the endotracheal tube without bucking, while responding and following verbal commands that allowed safe extubation. Also, while a few patients requested pain medication after surgery, most patients did not show signs of distress due to pain, confusion, or excitation. The smooth and rapid recovery from anesthesia without any sign of respiratory depression, and other side effects such as nausea, vomiting, and shivering are significant benefits for an anesthetic used in clinical practice.

The invention now being fully described, it will be apparent to one of ordinary skill in the art that various changes and modifications can be made without departing from the spirit or scope of the invention.

I claim:

1. A method of modulating the autonomic nervous system responses to noxious stimulation, comprising the step of administering to a mammal a pharmaceutical composition comprising an adenosine compound at a dosage sufficient to attenuate the autonomic nervous system responses to noxious stimulation, wherein said adenosine compound is selected from the group consisting of adenosine, adenosine monophosphate, adenosine diphosphate, and adenosine triphosphate.

2. The method of claim 1, wherein said method further comprises the step of administering a compound selected from the group consisting of an opioid, nitrous oxide, a benzodiapine, and a halogenated anesthetic compound at a dosage sufficient to attenuate the autonomic nervous system responses to noxious stimulation.

3. The method of claim 1, wherein the mammal is a human.

4. The method of claim 1, wherein the dosage administered is from about 5 µg/kg/min to about 5000 µg/kg/min.

5. The method of claim 1, wherein said noxious stimulation is selected from the group consisting of surgical stimulation and hypothermia.

* * * * *

UNITED STATES PATENT AND TRADEMARK OFFICE
CERTIFICATE OF CORRECTION

PATENT NO. : 5,679,649
DATED : Oct. 21, 1997
INVENTOR(S) : Atsuo F. Fukunaga

It is certified that error appears in the above-identified patent and that said Letters Patent is hereby corrected as shown below:

Column 3, Line 21, After "stimulation ", Delete ".", and add--as indicated by the abbreviation ES--.

Column 11, Line 58, Change "32", To read --362--.

Column 22, Claim 1, Line 34, Change "modulating", To read --attenuating--.

Signed and Sealed this

Thirty-first Day of March, 1998

Attest:

BRUCE LEHMAN

Attesting Officer

Commissioner of Patents and Trademarks